United States Patent [19] [11] 4,203,904
Reynolds, Jr. [45] May 20, 1980

[54] ALKYLATION OF ANILINE WITH A LACTONE IN THE PRESENCE OF A BASE

[75] Inventor: Richard N. Reynolds, Jr., Albany, Calif.

[73] Assignee: Chevron Research Company, San Francisco, Calif.

[21] Appl. No.: 928,481

[22] Filed: Jul. 27, 1978

[51] Int. Cl.$^2$ ............... C07D 307/32; C07D 207/26; C07D 333/36
[52] U.S. Cl. ................ 260/343.6; 260/326.5 FL; 549/63
[58] Field of Search ............... 260/343.6, 332.3 AL, 260/326.5 FL, 577

[56] References Cited

U.S. PATENT DOCUMENTS

| 3,002,976 | 10/1961 | Janssen | 260/332.3 R |
| 3,097,206 | 7/1963 | Zirkle | 260/332.3 R |
| 3,714,153 | 1/1973 | Martel et al. | 260/343.6 |
| 3,786,097 | 1/1974 | Karrer | 260/577 |
| 3,833,607 | 9/1974 | Enders et al. | 260/343.6 |
| 3,914,311 | 10/1975 | Coulson | 260/577 |
| 3,933,860 | 1/1976 | Chan | 260/343.6 |

FOREIGN PATENT DOCUMENTS 659483  10/1951  United Kingdom ................ 260/343.6

Primary Examiner—Alan L. Rotman
Assistant Examiner—Natalia Harkaway
Attorney, Agent, or Firm—J. A. Buchanan, Jr.; D. A. Newell; T. G. DeJonghe

[57] ABSTRACT

A process for producing a lactone-substituted aniline wherein a 3-halo-tetrahydro-2-oxofuran is reacted with an aniline in the presence of water and a base at a temperature between 80° and 160° C. and wherein the base is added at a sufficiently slow rate so that the pH does not exceed about 7.5.

9 Claims, No Drawings

ALKYLATION OF ANILINE WITH A LACTONE IN THE PRESENCE OF A BASE

RELATED APPLICATION

This application is related to my earlier application entitled ALKYLATION OF ANILINE WITH A LACTONE IN THE PRESENCE OF WATER, Ser. No. 847,503, filed Nov. 1, 1977, now U.S. Pat. No. 4,165,322, the disclosure of which application is incorporated herein by reference.

BACKGROUND OF THE INVENTION

According to the present invention, a process is provided for reacting an aniline compound with a lactone. This reaction is referred to herein as an "alkylation" reaction. The term "alkylation" is thus used herein to refer to an addition reaction between an aniline and a lactone.

The compounds prepared in accordance with the process of the present invention are especially useful as fungicides.

Commonly assigned U.S. Pat. No. 3,933,860 discloses the preparation of lactone-substituted compounds wherein in a first step the following reaction is carried out:

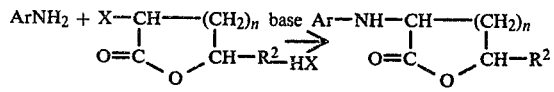

As can be seen from the examples in U.S. Pat. No. 3,933,860, the aniline reaction is carried out in the absence of water. Thus, in Example 1, 3,4-dichlorobenzeneamine (which may also be called 3,4-dichloroaniline) is reacted with 3-bromotetrahydro-2-oxofuran (which may also be called alpha-bromo-gamma-butyrolactone) at 110° to 145° C. to give a solid mixture of about equimolar amounts of 3,4-dichlorobenzeneamine hydrobromide salt and N-(tetrahydro-2-oxo-3-furanyl)3,4-dichlorobenzeneamine [which may also be called 3-(N-3,4-dichlorophenylamino)-gamma-butyrolactone]. The mixture thus obtained was treated with dichloromethane and filtered to separate the salt as a solid. The filtrate was evaporated to thereby remove the dichloromethane and yield the desired aniline-lactone reaction product.

In Example 2 of U.S. Pat. No. 3,933,860, 0.1 mol 2,6-dimethylbenzeneamine, 0.1 mol 3-bromotetrahydro-2-oxofuran, 0.1 mol sodium carbonate and 150 ml dimethylformamide were heated as a slurry to 125°–140° C. The reaction time was 21 hours. After the reaction was complete, the reaction mixture was diluted with water at room temperature and then extracted with benzene to remove the desired aniline-lactone product. The organic phase, that is, the benzene phase, was processed to separate the aniline-lactone product from the benzene phase.

SUMMARY OF THE INVENTION

According to the present invention, a process is provided for making a compound of the formula

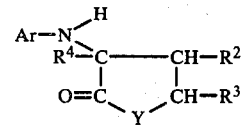

wherein
Ar is derived from the anilino group and is phenyl or phenyl substituted with the same or different substituents selected from 1 to 5 alkyl or alkoxy groups of 1 to 4 carbon atoms; 1 to 2 fluoro, chloro, iodo or bromo, and 1 nitro;
$R^2$, $R^3$ and $R^4$ are hydrogen or alkyl of 1 to 4 carbon atoms; and
Y is O, S or N—R where R is H or alkyl of 1 to 4 carbon atoms.

The process comprises:
contacting and reacting a 3-halo lactone or 3-halo thiolactone compound of the formula

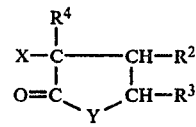

wherein X is chloro, iodo or bromo; and Y, $R^2$, $R^3$ and $R^4$ are as previously defined;
with an aniline compound unsubstituted or substituted in the aromatic ring with the same or different substituents selected from 1 to 5 alkyl or alkoxy groups of 1 to 4 carbon atoms; 1 to 2 fluoro, chloro, iodo or bromo; and 1 nitro, in the presence of water, a base, and optionally an inert organic solvent, in a reaction zone at a temperature between 80° and 160° C. to form the compound of Formula I, and wherein the base is gradually added to the reaction zone so as to maintain the pH below about 7.5.

Among other factors, the present invention is based on my finding that unexpectedly high yields of the alkylated aniline are obtained when the reaction is carried out with gradual addition of an alkali metal carbonate or hydrosulfite, such as sodium carbonate, sodium bicarbonate, or sodium hydrosulfite, compared to yields obtained when such bases are added to the reaction all at the beginning, or compared to no base at all.

In the present invention, preferably, the base is gradually and continuously or substantially continuously added during the alkylation reaction. Thus, the aniline or aniline-type reactant and the lactone or lactone-type reactant can be charged to the reaction vessel and the base then added steadily as the reaction progresses, but with the base being added sufficiently slowly so that the pH preferably does not exceed about 7.5. A relatively small amount of the total base to be used during the course of the alkylation reaction can be present when the reactants are initially added to the reaction vessel in the case of a batch-type reaction, but preferably the base is commenced to be added to the combined aniline and lactone after or just as the temperature is raised to the reaction temperature of preferably 110° to 130° C. Then additional quantities of the base are added to the reaction zone as the reaction progresses, for example by drop-wise addition if the reaction is on a small scale, and by larger portions or at a higher rate if the process is on a larger scale.

If the reaction is carried out continuously by a continuous feed of the reactants to the reaction zone, the base is also continuously added.

In any case, it is preferred that the base be added at a rate to maintain the pH in the zone nearly neutral or at a lower pH down to the pH of the aniline hydrobromide salt present in the system, for example at a pH of about 1.0 to 7.5. More preferably, the pH is maintained by the gradual base addition at about 1.0 to 7 and, most preferably, at about 1.0 to 6.5.

Suitable bases include organic bases such as pyridine or N,N-dimethylaniline and inorganic bases such as alkali metal carbonates, e.g., sodium carbonate, potassium carbonate, and calcium carbonate. Also suitable are sodium bicarbonate, sodium acetate and sodium hydrosulfite. The inorganic bases sodium carbonate and sodium hydrosulfite have been found to be advantageous bases for use in the present process, especially sodium carbonate.

According to a preferred embodiment of the present invention, the lactone reactant is one wherein X is chloro or bromo, especially bromo, Y is O or S and $R^2$, $R^3$ and $R^4$ are hydrogen or methyl; and the aniline reactant is a 2,6-substituted aniline compound wherein the substituents at the 2- and 6-positions are methyl, ethyl or propyl. The terminology "hydrogen or methyl" means $R^2$, $R^3$ and $R^4$ may be the same or different. Preferably $R^2$, $R^3$ and $R^4$ are hydrogen.

Preferably the reaction is carried out in the absence of an organic solvent, that is, the reaction is carried out neat. When a solvent is used in the process of the present invention, it should be an organic solvent which is inert to reaction with aniline and with halolactones, under the process conditions. Thus, 1,2-dichloroethane has been found not to be suitable. Also, the solvent should be substantially immiscible in water, but preferably form an azeotrope for later removal of water.

Particularly preferred solvents for the alkylation reaction of the present invention include aromatic hydrocarbons such as benzene, toluene, xylene and haloaromatics such as chlorobenzene and chloronaphthalenes.

The alkylation reaction may be carried out at 50° to 200° C. However, I have found that 80° to 160° C. is preferable. Particularly preferred temperatures for the process of the present invention are 90° to 140° C.

Preferred pressures are atmospheric to 100 psig.

Preferred ratios for the feed constituents to the process of the present invention are 1 mol of the lactone, 0.8 to 6 mols of the aniline, 1 to 40 mols of water and 0 to 30 mols of the inert organic solvent. More preferred ratios for the feed constituents to the alkylation reaction of the present invention are 1 mol of the lactone, 0.8 to 1.1 mols of the aniline, 7 to 13 mols of the water and 0 to 2.3 mols of the inert organic solvent. The quantity of base is preferably in the range of 0.9 to 1 equivalent of base per mol of the aniline.

According to a particularly preferred embodiment of the present invention, a process is provided for making N-(tetrahydro-2-oxo-3-furanyl)-2,6-dimethylbenzeneamine [which may also be called 3-(N-2,6-dimethylphenylamino)-gamma-butyrolactone], which comprises reacting 3-halo-tetrahydro-2-oxofuran, wherein the halo group is bromo or chloro, with 2,6-dimethylbenzeneamine (which may also be called 2,6-dimethylaniline), in the presence of water, a base, and optionally an inert organic solvent, at a temperature between 80° and 160° C. to form the N-(tetrahydro-2-oxo-3-furanyl)-2,6-dimethylbenzeneamine, and wherein the base is gradually added to the reaction zone so as to maintain the pH below about 7.5.

Preferably the base is sodium carbonate. Preferably the halo group of the lactone reactant is bromo. Preferably no solvent is employed; optionally an inert organic solvent is used, such as toluene, and preferably the reaction temperature is between 90° and 140° C.

Preferred ratios for the above-mentioned feed constituents to the reaction zone are 1 mol of the 3-halo-tetrahydro-2-oxo-furan, 0.8 to 1.1 mols of 2,6-dimethylbenzeneamine, 7 to 13 mols water, 0 to 2.3 mols toluene, and 0.4 to 0.5 mol of sodium carbonate added gradually to the reaction mixture (so as to maintain an acid pH).

EXAMPLES

Example 1

The reaction was carried out in the presence of solvent and slow base addition.

A 500-ml, 3-necked, round-bottom flask equipped with a stirrer, thermometer, condenser with a Dean-Stark trap, and a dropping funnel, was charged with 49.7 g (0.41 mol) of 2,6-dimethylbenzeneamine, 67.9 g (0.41 mol) of 3-bromotetrahydro-2-oxofuran and 134 g of toluene. The solution was heated to 120° C. Then a solution of 22.8 g (0.22 mol) of sodium carbonate in 60 ml of water was added at an initial rate of 0.16 equivalent per hour. After 3 hours, 0.6 equivalent had been added at a temperature in the range of 110°-115° C. Carbonate addition was continued at a slower rate, until all was added at a total time of 345 minutes. After another 10 minutes, the reaction mixture was cooled to room temperature and was allowed to stand for 16 hours.

Water, 60 ml, was added to the crude reaction mixture, which was then heated to 60° C. to dissolve solids. The two liquid phases were separated. The organic layer was washed once with 40 ml of hot water, twice with 80-ml portions of 5% hydrochloric acid. The combined acid extracts were back-extracted with 25 ml dichloromethane, which was then added to the organic phase. The resulting organic solution was stripped to give 87 g of a solid material.

Analysis of the crude solid product showed it to contain 68.6 g (81.7% yield based on 2,6-dimethylbenzeneamine feed) of N-(tetrahydro-2-oxo-3-furanyl)-2,6-dimethylbenzeneamine and 2.6 g of 2,6-dimethylbenzeneamine (95% conversion).

Comparative Example 2

This reaction was carried out in the presence of solvent and faster base addition (pH above about 7.5 initially).

The same equipment as used for Example 1 was charged with 82.5 g (0.5 mol) of 3-bromotetrahydro-2-oxofuran, 60.5 g (0.5 mol) of 2,6-dimethylbenzeneamine, 100 ml of toluene and 20 ml of water. The mixture was heated to 88° C. and a solution of 26.5 g (0.25 mol) of sodium carbonate was dissolved in 80 ml of water was added dropwise over 60 minutes. The resulting mixture was stirred at reflux for about 20 hours.

After cooling to room temperature, the organic phase was separated from the aqueous phase. The organic layer was washed four times with 50-ml portions of 5% hydrochloric acid. The organic layer was then stripped of solvent to yield 41.9 g of an oil. Analysis of this crude product gave a 29.5% yield of N-(tetrahydro-2-oxo-3-furanyl)-2,6-dimethylbenzeneamine.

In this Example 2, the pH was not maintained below 7.5. However, in Example 1, wherein the yield was 81.7% by weight, the sodium carbonate was added sufficiently slowly so that the pH did not exceed about 7.5.

Example 3

This reaction was carried out neat and with slow base addition. To a 500-ml flask was added 60.6 g (0.5 mol) of 2,6-dimethylbenzeneamine and 90.8 g (0.55 mol) of 3-bromotetrahydro-2-oxofuran.

The solution was heated to 120° C. Then a solution of 26.5 g (0.25 mol) of sodium carbonate in 100 ml of water was added at an initial rate of 7.9 g sodium carbonate per hour. After 110 minutes, 55% of the sodium carbonate solution had been added at a temperature in the range of 105°-112° C. Sodium carbonate addition was then continued at a rate of 4.1 g sodium carbonate per hour for 160 minutes until all was added. Heating was continued 30 minutes at 105° C. Total sodium carbonate addition time was 4.5 hours. Total time at 105°-120° C. was 5.0 hours. The reaction mixture was cooled to room temperature and was allowed to stand 16 hours. With this slow addition of sodium carbonate base, the pH was maintained less than about 7.5. Generally, the pH was below about 6.5 and above about 1.0, as determined from other experimental work which was carried out wherein the pH was substantially continuously monitored by drawing off small samples as the reaction progressed.

In order to work up the reaction product from the above alkylation reaction, about 100 ml of toluene was added to the crude product reaction mixture and then the mixture was heated to 65° C. to dissolve solids.

The resulting two liquid phases were separated. The organic layer was washed three times (27-, 27- and 9-ml portions) with a 5% aqueous ammonia solution, twice with 40-ml portions of 5% hydrochloric acid, and once with 25 ml of water. All washing steps were done at a temperature in the range of 50° to 60° C. to prevent crystallization of the product. The resulting organic solution was stripped to give 90.7 g of a tan solid.

Analysis of the crude solid product showed it to contain 83.1 g (81.1% yield based on 2,6-dimethlybenzeneamine feed) of N-(tetrahydro-2-oxo-3-furanyl)-2,6-dimethylbenzeneamine.

Example 4

This reaction was carried out neat and with all of the base added at the start of the reaction. In this run, 0.5 mol of 2,6-dimethylbenzeneamine, 0.5 mol of 3-bromotetrahydro-2-oxofuran, 0.25 mol of sodium carbonate and 100 ml of water were added to a flask. As in the other examples, the reaction flask was equipped with a mechanical stirrer, thermometer and condenser. The solution in the flask was heated to reflux, 102° C.

The reaction was followed at time intervals by drawing samples which were checked for pH. The initial pH was 8.4, and then after the first several minutes of reaction time the pH remained at about 3.1 to 3.5.

The total reaction time was about 4 hours.

The approximate yield of product N-(tetrahydro-2-oxo-3-furanyl)-2,6-dimethylbenzeneamine was 25.4 mol percent.

What is claimed is:

1. A process for making a compound of the formula

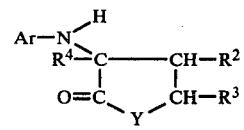

wherein
Ar is phenyl or phenyl substituted with the same or different substituents selected from 1 to 5 alkyl or alkoxy groups of 1 to 4 carbon atoms; 1 to 2 fluoro, chloro, iodo or bromo; and 1 nitro;
$R^2$, $R^3$ and $R^4$ are hydrogen or alkyl of 1 to 4 carbon atoms; and
Y is O, S or N—R where R is H or alkyl of 1 to 4 carbon atoms,
which comprises:
contacting and reacting a compound of the formula

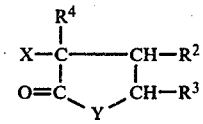

wherein X is chloro, iodo or bromo; Y, $R^2$, $R^3$ and $R^4$ are as previously defined;
with an aniline compound, unsubstituted or substituted in the aromatic ring with the same or different substituents selected from 1 to 5 alkyl or alkoxy groups of 1 to 4 carbon atoms; 1 to 2 fluoro, chloro, iodo or bromo; and 1 nitro, in the presence of water and an inorganic base in a reaction zone at a temperature between 80° and 160° C. to form the compound of Formula I, and wherein the base is added sufficiently slowly to the reaction zone so that the pH does not exceed about 7.5.

2. A process in accordance with claim 1 wherein the base is added at a rate so as to maintain the pH between about 1 and 7.

3. A process in accordance with claim 2 wherein the base is sodium carbonate.

4. A process in accordance with claim 1 wherein: X is chloro or bromo; Y is O or S; $R^2$, $R^3$ and $R^4$ are hydrogen or methyl; and the aniline compound is a 2,6-substituted aniline compound wherein the substituents at the 2- and 6-position are methyl, ethyl, or propyl.

5. A process in accordance with claim 2 wherein X is bromo.

6. A process for making N-(tetrahydro-2-oxo-3-furanyl)-2,6-dimethylbenzeneamine which comprises reacting 3-halotetrahydro-2-oxofuran, wherein the halo group is bromo or chloro, with 2,6-dimethylbenzeneamine in the presence of water and a base at a temperature between 80° and 160° C. to form N-(tetrahydro-2-oxo-3-furanyl)-2,6-dimethylbenzeneamine, and wherein the base is gradually added to the reaction zone so as to maintain the pH below about 7.5.

7. A process in accordance with claim 6 wherein the halo group is bromo and the base is sodium carbonate.

8. A process in accordance with claim 7 wherein the temperature is between 90° and 140° C.

9. A process in accordance with claim 7 wherein the reaction of the 3-halo-tetrahydro-2-oxofuran with the 2,6-dimethylbenzeneamine is carried out in a reaction zone and with the ratio of feed constituents to the reaction zone comprising: one mol of the 3-bromotetrahydro-2-oxofuran, 0.8 to 1.1 mols 2,6-dimethylbenzeneamine, 7 to 13 mols water, and 0.4–0.5 mol sodium carbonate.

* * * * *